United States Patent
Sanchez-Martinez et al.

(10) Patent No.: US 9,775,420 B2
(45) Date of Patent: Oct. 3, 2017

(54) ATTACHMENT FOR EPILATOR AND EPILATOR

(71) Applicant: Braun GmbH, Kronberg (DE)

(72) Inventors: Pedro Sanchez-Martinez, Kronberg (DE); Ralf Klug, Eschborn (DE); Thomas Steiner, Trebur (DE)

(73) Assignee: Braun GmbH, Kronberg (DE)

( * ) Notice: Subject to any disclaimer, the term of this patent is extended or adjusted under 35 U.S.C. 154(b) by 323 days.

(21) Appl. No.: 14/253,948

(22) Filed: Apr. 16, 2014

(65) Prior Publication Data

US 2014/0309663 A1    Oct. 16, 2014

(30) Foreign Application Priority Data

Apr. 16, 2013   (EP) .................................. 13163905

(51) Int. Cl.
| | |
|---|---|
| *A61B 17/50* | (2006.01) |
| *A45D 26/00* | (2006.01) |
| *A61H 15/00* | (2006.01) |
| *A46B 15/00* | (2006.01) |
| *A61B 17/00* | (2006.01) |

(52) U.S. Cl.
CPC ..... *A45D 26/0028* (2013.01); *A45D 26/0057* (2013.01); *A46B 15/0055* (2013.01); *A46B 15/0075* (2013.01); *A61H 15/0085* (2013.01); *A45D 2026/008* (2013.01); *A61B 2017/00752* (2013.01)

(58) Field of Classification Search
CPC ............ A45D 26/0023; A45D 26/0028; A45D 26/0033; A45D 26/0038; A45D 26/0047; A45D 26/0052; A45D 26/0057; A45D 2026/008; A61B 2017/00752; A61B 2018/00476

USPC ......................................................... 606/133
See application file for complete search history.

(56) References Cited

U.S. PATENT DOCUMENTS

| | | |
|---|---|---|
| 2,400,227 A | 5/1946 | Julius |
| 5,041,123 A | 8/1991 | Oliveau et al. |
| | (Continued) | |

FOREIGN PATENT DOCUMENTS

EP    0921744    6/2002

OTHER PUBLICATIONS

European search report dated Aug. 6, 2013, 7 pages.

*Primary Examiner* — David C Eastwood
*Assistant Examiner* — Kankindi Rwego
(74) *Attorney, Agent, or Firm* — Ronald T. Sia; Kevin C. Johnson; Steven W. Miller

(57) ABSTRACT

The present disclosure is concerned with an attachment for an epilator or an epilator having an axle arranged for driven movement around a center axle axis, an end plate arranged at a first end of the axle for rotation together with the axle, the end plate having at least a first functional surface, a first clamping element having a functional surface, the first functional surface of the end plate being arranged face-to-face with the functional surface of the first clamping element, and the first clamping element being arranged for repeatedly being moved towards and away from the end plate such that repeatedly a closed position is obtained in which the two functional surfaces abut on each other, wherein the end plate is an outer part of the epilator or the attachment for an epilator.

16 Claims, 14 Drawing Sheets

(56) References Cited

U.S. PATENT DOCUMENTS

| | | | |
|---|---|---|---|
| 5,190,559 A * | 3/1993 | Gabion | A45D 26/0028 606/131 |
| 5,441,506 A | 8/1995 | Gabion et al. | |
| 5,857,903 A * | 1/1999 | Ramspeck | A45D 26/0028 452/82 |
| 2008/0269780 A1* | 10/2008 | Sanchez-Martinez | A45D 26/0028 606/133 |
| 2011/0306987 A1* | 12/2011 | Grieshaber | A45D 26/0028 606/133 |
| 2012/0022556 A1* | 1/2012 | Sanchez-Martinez | A45D 26/0028 606/133 |

* cited by examiner

ATTACHMENT FOR EPILATOR AND EPILATOR

FIELD OF THE INVENTION

The present invention is concerned with an attachment for an epilator or an epilator having a clamping head for clamping hairs.

BACKGROUND OF THE INVENTION

It is known that an epilator can be provided, in particular an epilator suitable for facial epilation, where clamping elements are arranged close to a housing edge of the epilator for precise treatment of small facial skin areas. Such an epilator is generally described in document EP 0 601 003 A1.

From U.S. Pat. No. 2,400,227 an epilator is known having an end plate that is located at the end face of the epilator and that cooperates with a single clamping element for forming a single gap between both that intermittently opens and closes all around the circumference of the clamping element and the end plate at once for extracting hair caught in-between.

It is an object of the present disclosure to provide an epilator or an attachment for an epilator that in particular is suitable for precise facial epilation and is improved over the known devices.

SUMMARY OF THE INVENTION

In accordance with one aspect there is provided an attachment for an epilator or an epilator comprising an axle arranged for driven movement around a centre axle axis, an end plate arranged at a first end of the axle for rotation together with the axle, the end plate having at least a first functional surface, a first clamping element having a functional surface, the first functional surface of the end plate being arranged face-to-face with the functional surface of the first clamping element, and the first clamping element being arranged for repeatedly being moved towards and away from the end plate such that repeatedly a closed position is obtained in which the two functional surfaces abut on each other, wherein the end plate is an outer part of the epilator or the attachment for an epilator.

In accordance with one aspect there is provided an epilator comprising an attachment as proposed and a handle for being held in the hand of a user, wherein the handle defines a holding axis that is inclined with respect to the centre axle axis

BRIEF DESCRIPTION OF THE DRAWINGS

The present disclosure will be further elucidated by a detailed description of example embodiments of an attachment for an epilator or an epilator, in particular with reference to figures. In the figures.

DETAILED DESCRIPTION OF THE INVENTION

Figure 1A:
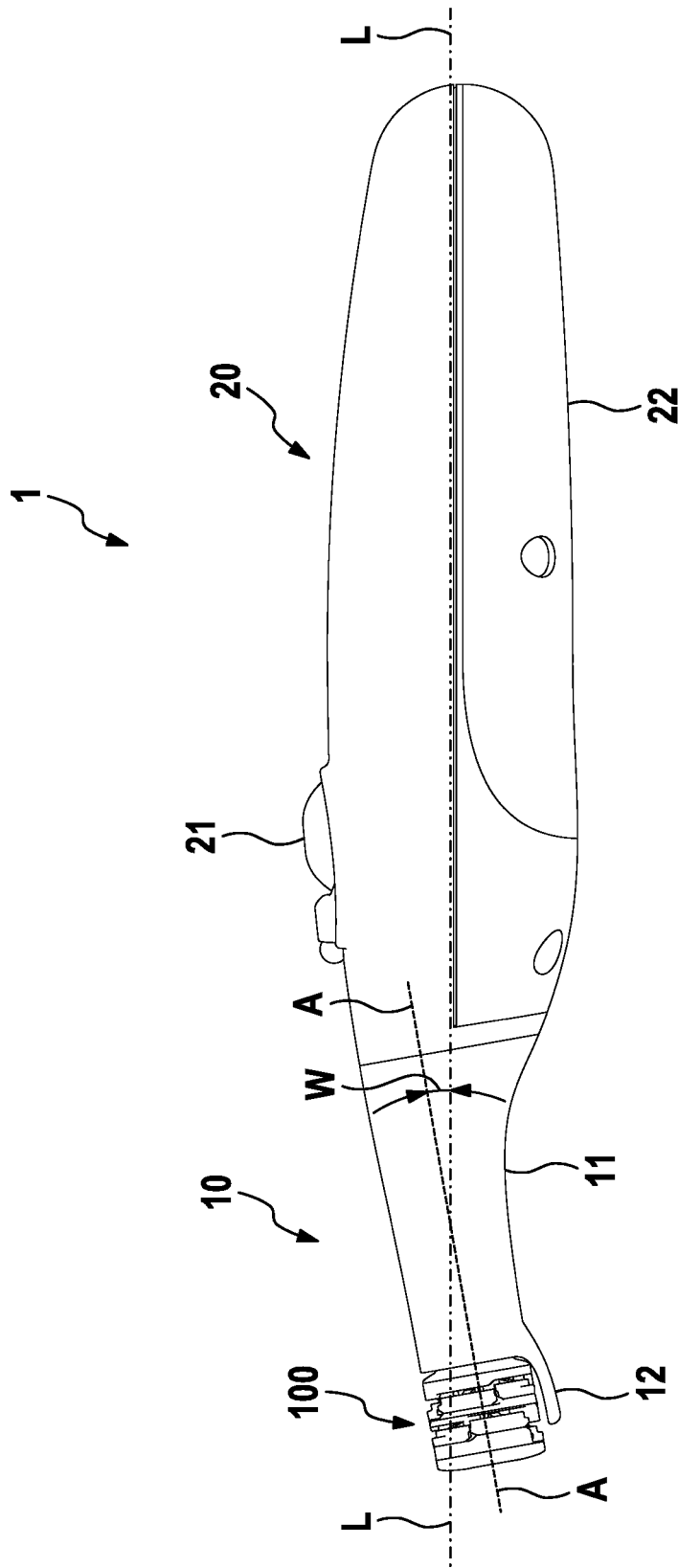
FIG. 1A is a depiction of an example embodiment of an epilator comprising an attachment.

In the following, terms will be introduced that may be used for a set of identical or at least similar features. E.g. the term "clamping element" will be used. Individual clamping elements will then be named "first clamping element", "second clamping element", etc. or "first additional clamping element", "second additional clamping element", etc., while it will be referred to the group comprising the first, second, etc. clamping elements as well as any additional clamping elements as "clamping elements".

It is noted that the following represents a detailed description of example embodiments of an epilator or an attachment for an epilator and that features shown together in one of the discussed embodiments are not to be interpreted as necessarily being meant to be only disclosed in the shown assembly. The skilled person would of course consider only those features as disclosed together that are relevant for a particular realization of an epilator or attachment for an epilator in accordance with the present disclosure and would discard others as long as this would not be in conflict with the gist and scope of the present disclosure. This shall mean that all features are to be considered as individually disclosed and that no compulsory connection is intended by describing two or more features together in any one of the example embodiments.

It is further noted that while the example embodiments shown in the figures have a certain number of particular features such as clamping elements, an epilator or an attachment for an epilator in accordance with the present disclosure may have, e.g., only one clamping element, may have two or any other number of clamping elements, etc.

Before a detailed description is presented with reference to the figures, a more general description of an epilator or an attachment for an epilator will follow.

Reference is made to the epilator or the attachment for an epilator as disclosed in the summary section above. As the end plate comprises the first functional surface that interacts with the functional surface of the first clamping element (thereby forming a pair of tweezers that can be closed for clamping hairs and eventually plucking these hairs from the skin) and as the end plate is an outer part of the epilator or attachment, the outer edge of the epilator or attachment can be realized very close to the first pair of tweezers, i.e. very close to the first gap between functional surfaces between which hairs can be clamped. In particular, as the end plate is an integral element (i.e. a single piece element) comprising an outer surface of the epilator or attachment (i.e. an outer surface intended for getting into contact with a user's skin or, in other words, a housing surface) and a first functional surface of a pair of tweezers, the end plate needs only to be as thick in axial direction as is needed to guarantee a structurally solid object that can withstand any clamping forces that may be applied onto the end plate during operation. Thus the end plate forms at one side thereof the end face or end housing face of the epilator/attachment and at the other side thereof a first functional surface for clamping hair together with a clamping element. The clamping force, as is known, shall keep a clamped hair clamped when it is plucked from the skin when the closed pair of tweezers is moved relatively to the skin. The end plate may be made from plastic, in particular a filled plastic, and a minimal axial thickness of 0.5 mm or 1.0 mm may be sufficient to ensure the structural stability of the end plate. An end plate made from metal may also be used in order to even further reduce the minimal thickness but this would increase the manufacturing costs and metal would also feel cold at the skin.

In some embodiments, the epilator or attachment further comprises a resilient element such as a spring that is resilient in axial direction (i.e. in a direction at least parallel to the centre axle axis), which resilient element is at one end (being distal to the end plate) arranged against a first stopper element that is fixed in axial relationship with respect to the axle, e.g. wherein the first stopper element is fixedly connected with the axle or with the housing (the latter implying that the axle is locked against axial movement). The other end of the resilient element may then abut on a pressure plate that has a functional surface (facing towards the end plate), which functional surface has an axially extending projection. The resilient element, while locked by the stopper element against axial movement, is thus able to provide a return force when being compressed in axial direction, i.e. when the pressure plate pushes against the other end of the resilient element.

In some embodiments, the epilator or attachment further comprises at least a first actuator associated with the first clamping element. The first actuator is then arranged to get at least intermittently into sliding contact with the functional surface of the pressure plate during operation. An end of the first actuator distal to the end plate may thus get into sliding contact at least with a part of the axial projection of the functional surface of the pressure plate. The first actuator is arranged for being moveable in axial direction towards (and away from) the end plate when it slides over the axial projection. The first actuator moves then the first clamping element towards the end plate such that the face-to-face arranged first functional surface of the end plate and the functional surface of the first clamping element move from an open position in which a gap having an axial width extends between them into the closed position in which they get into clamping contact. The axial projection may be higher in axial direction than the axial gap width and thus the solid structure of end plate, first clamping element and first actuator pushes the pressure plate axially away from the end plate, which in turn compresses the resilient element and thus builds up a clamping force between the closed functional surfaces due to the return force provided by the resilient element.

In some embodiments, a first spring element (that may extend in axial direction) is arranged between the end plate and the first clamping element such that the first spring element keeps the two functional surfaces in an open position while no other closing force overcomes the spring force of the first spring element. The first spring element may have a relatively low spring constant in comparison to the spring constant of the resilient element. The spring element may e.g. be realized as a coil spring and may further be arranged such that longer hairs may be clamped in between windings of the coil spring and thus the first spring element may support the clamping and plucking of hairs.

In some embodiments, at least a second clamping element is provided, which second clamping element may have a functional surface that is face-to-face arranged with a second functional surface of the end plate. The second functional surface of the end plate may be circumferentially and, optionally, also axially be displaced from the first functional surface of the end plate. Likewise, the second clamping element may be circumferentially and, optionally (in its open position), also be axially displaced from the first clamping element. The second clamping element may be associated with a second actuator. In some embodiments, a third clamping element may be present, additionally a fourth clamping element may be present, optionally a fifth clamping element may be present, etc. Thus a first group of clamping elements may comprise 1 to 5 clamping elements and further such groups may be axially displaced to the first group provided. In some embodiments, the clamping elements may be arranged so as to span full 360 degrees (potentially with small gaps due to manufacturing tolerances). Alternatively, the clamping elements may be arranged to span less than 360 degrees so that an angular distance is between the circumferentially offset clamping elements, e.g. each of five clamping elements may span 50 degrees and a distance of 22 degrees may thus be between neighboring clamping elements. Each clamping element may be associated with its own actuator in a one-to-one manner. The end plate comprises thus several functional surfaces each being axially displaced from each other, wherein the axial displacement of the functional surfaces of the end plate is provided by a different axial projections from the end plate or a different thickness of a portion of the end plate for each functional surface.

In some embodiments, a closure element is present that may be axially and angularly locked with respect to the end plate, e.g. by an axially extending connection structure which may be realized at least in part by an axially extending pin. In some embodiments, the axially extending connection structure may comprise two or more axially extending pins. The closure element may in particular have at least a first guiding structure for guiding the first actuator; optionally the closure element may have a guiding structure for each actuator. In some embodiments, the first guiding structure may be realized by a part of the axially extending connection structure, e.g. an axially extending pin.

In some embodiments, the epilator or attachment further comprises a centre plate that may be axially and angularly locked with respect to the end plate by an axially extending connection structure, e.g. by at least a first axially extending pin. In such an embodiment, the closure element may be axially and angularly locked with respect to the centre plate by means of an axially extending connection structure. In some embodiments, the centre plate has two or even more axially extending pins for coupling the centre plate with the end plate, where the axially extending connection structure may thus be integrally realized with the centre plate. The centre plate may have a functional side facing towards the pressure plate on which at least a first functional surface is provide. In some embodiments, a first additional clamping element is provided that has a functional surface that is face-to-face arranged with the first functional surface of the centre plate. A first additional actuator may be associated with the first additional clamping element. As was said before, further additional clamping elements (that each may be associated with their own additional actuator and each having a functional surface that may be face-to-face arranged with a respective functional surface of the centre plate) may be present and optionally each of these additional clamping elements may be circumferentially and optionally also axially be displaced from each other as was mentioned before for the clamping elements cooperating with the end plate. Thus, by using a centre plate, a further circumferential arrangement of one or more additional clamping elements can be provided. In some embodiments, the centre plate may be axially and angularly locked by axially extending pins coupling the centre plate with the closure element. In such an assembly, the end plate, the centre plate, and the closure element are rigidly connected with each other and provide a frame structure for the clamping elements and actuators.

In some embodiments, at least the first clamping element and the first actuator are manufactured as an integral element. This integral element may in particular be made by a plastic injection molding process, where enforced plastic material (e.g. filled with glass fibers) may be used.

In some embodiments, the pressure plate has a first angular position around the axle when the axle is clockwise rotated and a second angular position around the axle when the axle is counterclockwise rotated. This enables to shift the closing point for both rotation directions to the same angular position with respect to a fixed housing.

FIG. 1A is a depiction of an example embodiment of an epilator 1 in accordance with the present disclosure. The epilator 1 may in particular be suitable for epilation of small areas such as facial skin areas, e.g. the eye-brows or skin areas near the nose. The epilator 1 has an attachment 10 having a clamping head 100 and a handle 20. The handle 20 is arranged for being held in a user's hand such that it then extends along a holding axis L (which coincides with the longitudinal extension axis of the handle 20). The handle 20 may comprise a switch 21 for switching the epilator 1 on and off and/or for switching the rotation direction of the clamping head (i.e. switching between clockwise and counterclockwise rotation). The handle 20 may be intended for being held such that a thumb of a user can work the switch 21. An elastomeric surface 22 may be arranged opposite the switch 21 for enhanced anti-slip properties. The attachment may have a tubular housing 11 and may additionally have a protection cap 12 for covering a side of the clamping head 100. The clamping head 100 is arranged for epilating hairs at a lateral side of the attachment 10. In some embodiments, the attachment 10 may extend along a centre axis A that is inclined with respect to the holding axis L such that in operation, when the functional side (i.e. the epilating side) of the clamping head 100 is aligned with the skin of a user, the handle 20 then projects away from the skin, which eases operation of the epilator in contrast to an epilator that completely extends along a single axis. The inclination angle W between the holding axis L and the centre axis A may be in the range of between about 2 degrees to about 30 degrees. In some embodiments, the attachment 10 is arranged for being repeatedly detachable from and attachable to the handle 20 such that the attachment 10 can be replaced by a new attachment in case it is worn out or can be exchanged with another functional attachment such as a brush attachment that may comprise a brush arranged for driven rotation or driven oscillation or a massage attachment, an exfoliation attachment, etc. The attachment 10 and the handle 20 may then also each comprise cooperating coupling structures for detachably coupling both parts together such as cooperating snap elements (e.g. a snap hook on one side and a cooperating undercut on the other side). The snap elements provide a snap fit connection between handle and attachment that may be snapped together and released from each other by simple movement in the direction along the axis of rotation of the clamping elements (without need for pressing a snap release button).

In accordance with the introductory paragraph above it is stated that e.g. the elastomeric surface 22 or the protection cap 12 are of course features that may obviously be chosen or discarded by a skilled person and thus are not to be considered as only disclosed in connection with each other or even in connection with all the other features shown in FIG. 1A. Such features can be discarded without even influencing the gist of the present invention. Besides some particular further examples below, it will not specifically be indicated for all discussed features that they are to be considered as individually disclosed as this should be obvious to the skilled person and also the whole disclosure would become practically illegible.

Figure 1B:
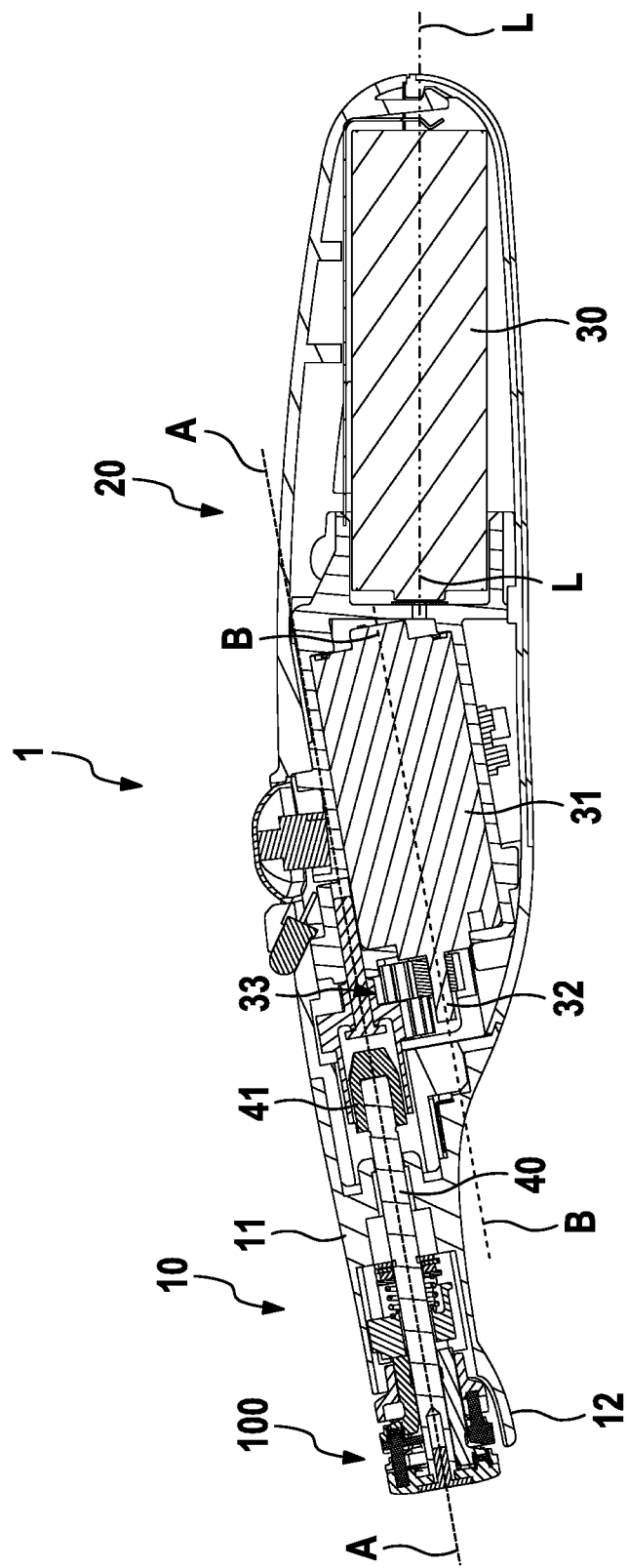
FIG. 1B is a longitudinal cross-sectional cut through the center of an epilator as shown in FIG. 1A.

FIG. 1B is a longitudinal cross-sectional cut through the epilator 1 shown in FIG. 1A. The handle 20 may comprise an energy source 30 such as a battery or a rechargeable accumulator that may be electrically coupled to a drive unit 31 such as a DC motor. The longitudinal extension axis of the energy source 30 may be parallel to the holding axis L. The drive unit 31 may comprise a drive axle 32 that in some embodiments extends along a drive axle axis B that is parallel or identical to the centre axis A of the attachment 10 (and thus would be inclined against the holding axis L in those embodiments where the holding axis L is inclined against the centre axis A of the attachment 10). The handle 20 may further comprise a gear unit 33 for coupling the drive axle 32 of the drive unit 31 with an axle 40 of the attachment 10 such that in operation the axle 40 is driven into motion. The axle 40 may comprise an axle connector element 41 via which the axle 40 is coupled to the gear unit 33.

Figure 2A:
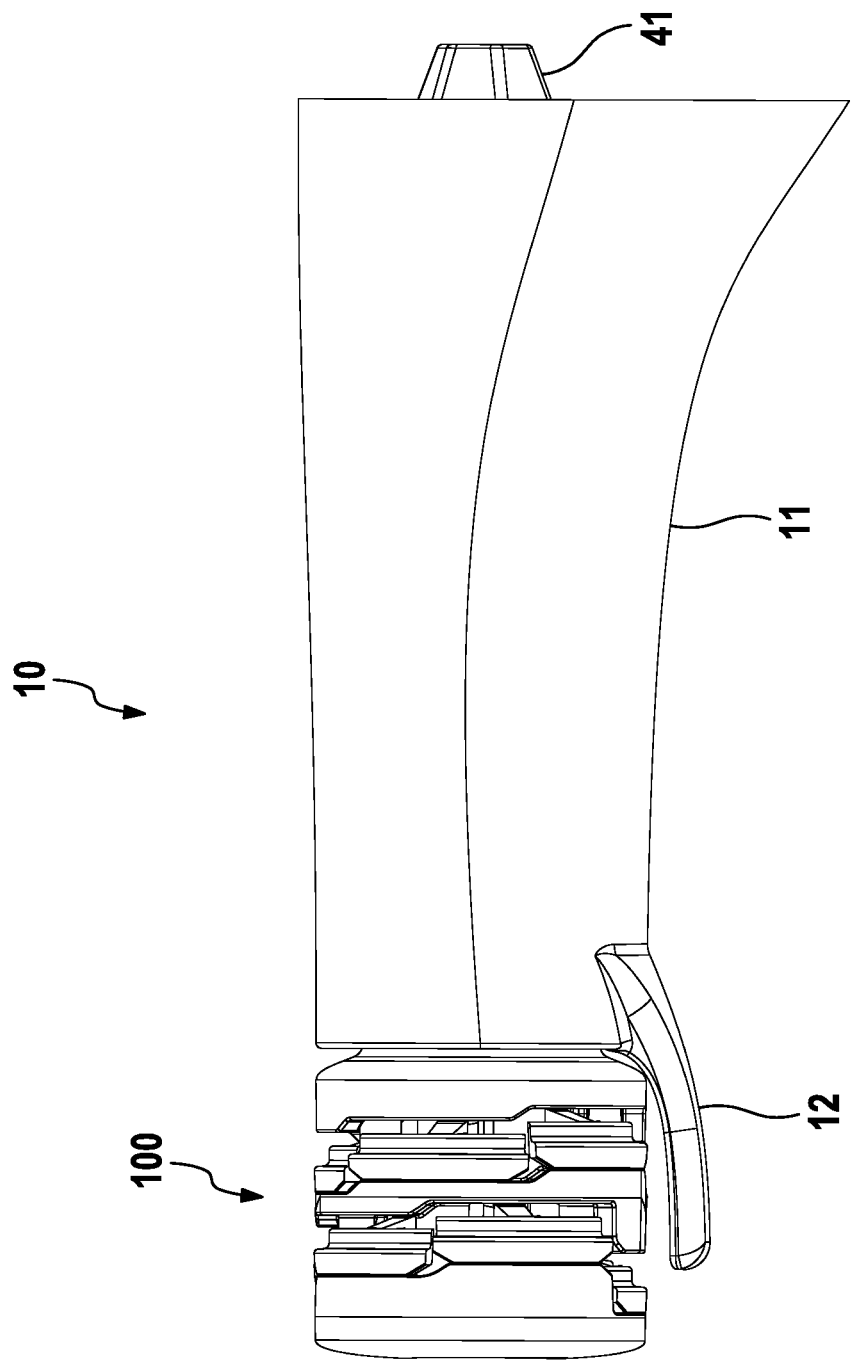
FIG. 2A is a depiction of an example embodiment of an attachment for an epilator.

FIG. 2A is a depiction of an attachment 10 shown in a detached state. The same features as in FIGS. 1A and 1B are indicated by the same reference numerals.

Figure 2B:
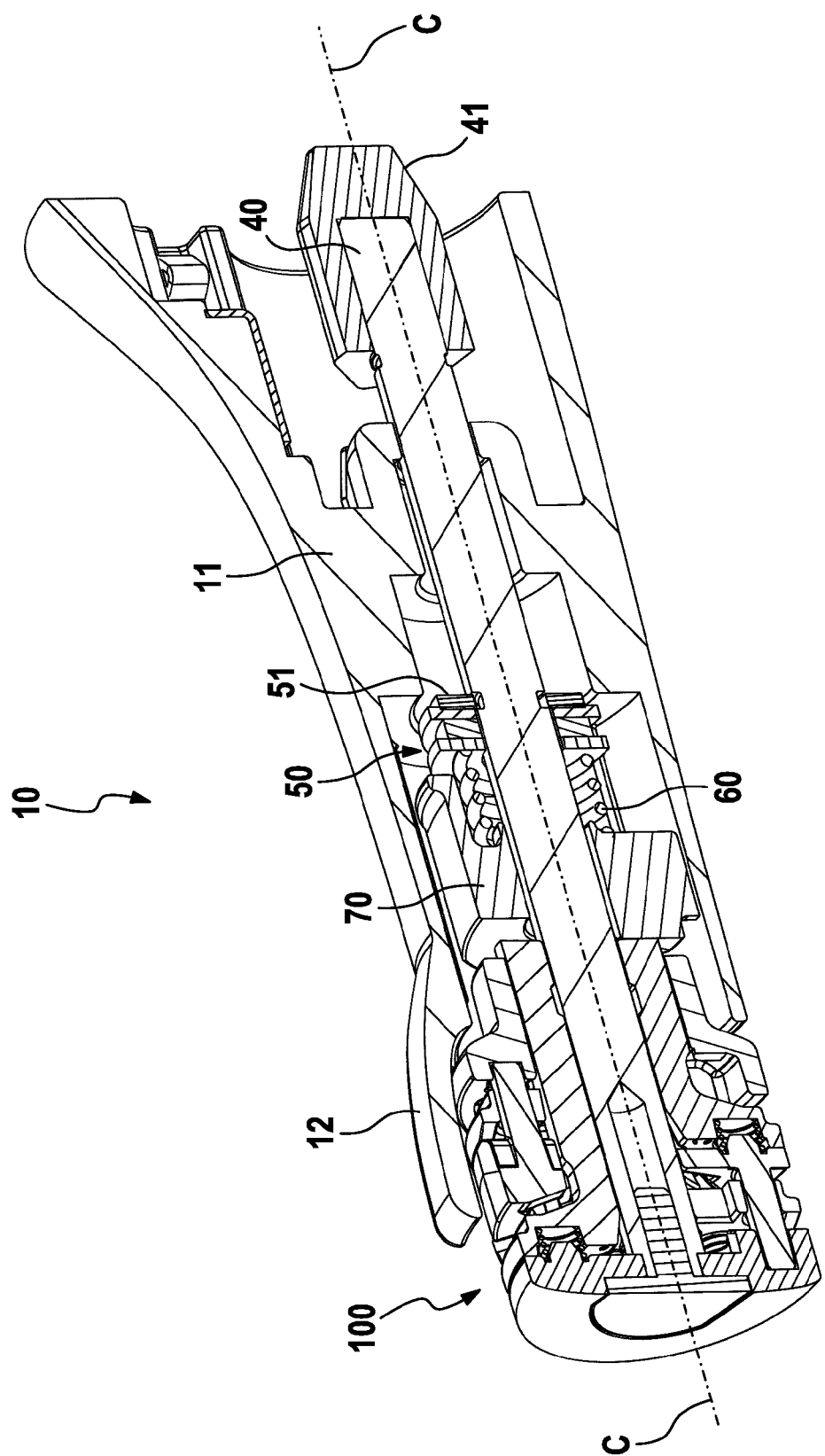
FIG. 2B shows a longitudinally cut open attachment for an epilator as shown in FIG. 2A.

FIG. 2B is a longitudinal cross-sectional cut through the attachment 10 shown in FIG. 2A. The attachment 10 comprises a hollow, essentially tubular housing 11, a clamping head 100, a protection cap 12, and an axle 40 having a centre axle axis C that may coincide with the centre axis A of the attachment 10 as indicated in FIGS. 1A and 1B. The axle 40 is supported by a bearing 50; in some embodiments, at least two bearings located at different axial positions are provided for improved stabilization of the centre axle axis C of the axle 40. In the shown example embodiment, the bearing 50 is fixed in axial positional relationship with the axle 40 by a locking element 51, which—as will be explained further below in more detail—also serves to close force transmission. Further, the axially locked bearing 50, 51 here also serves as a first stopper element. In some embodiments, the bearing may be arranged elsewhere and the first stopper element may be realized by a locking element locked on the axle 40 or the first stopper element may be realized by a projection of the housing 11. A resilient element 60 being elastic in axial direction (i.e. in direction of the centre axle axis C) abuts with a first end on the bearing 50 that here realizes the first stopper element together with the locking element 51. The resilient element 60 has a spring constant, i.e. the resilient element 60 provides a return force when being axially compressed. A second end of the resilient element 60 in axial direction abuts on a backside of a pressure plate 70. The resilient element 60 may be realized by a spring such as a coil spring or a disc spring (or stack of disc springs). The axle 40 is arranged for driven rotation around the centre axle axis C and in an attached state of the attachment 10 the axle 40 can be driven into rotation by a drive unit to which the axle 40 may be coupled via a coupling element 41.

Figure 3A:
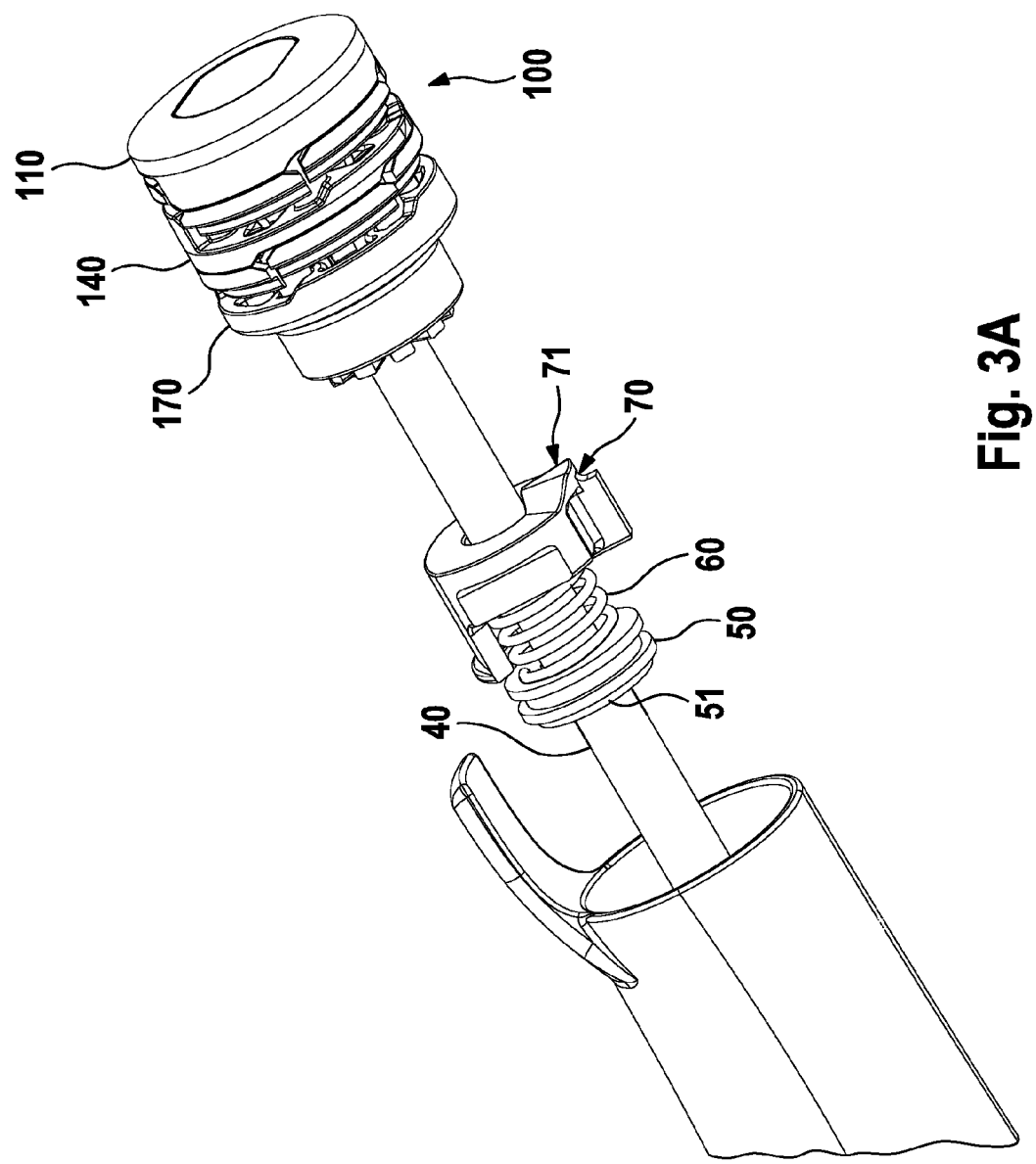
FIG. 3A is a perspective view onto an example embodiment of a clamping head in accordance with the present disclosure.

FIG. 3A is a side view onto an example embodiment of a clamping head 100 mounted on an axle 40 together with an axially locked bearing 50 realizing the first stopper element, a resilient element 60 and a pressure plate 70. The clamping head 100 comprises here an end plate 110, a centre plate 140, and a closure element 170. Also with reference to FIGS. 3B and 3C, the clamping head 100 comprises a set of five clamping elements 120A, 120B, etc. (i.e. a first clamping element, a second clamping element, etc.) that are circumferentially and axially displaced from each other. As will be also explained with reference to FIGS. 4 and 6 further below, the end plate 110 has then five functional surfaces (i.e. a first functional surface, s second functional surface, etc.) of which each is arranged face-to-face with a functional surface of a different one of the clamping elements 120. The axial functional surfaces extend in a plane essentially perpendicular to the centre axle axis. In the shown embodiment, the five functional surfaces of the end plate 110 span essentially 360 degree, so that each functional surface spans about 72 degrees. E.g. the first functional surface of the end plate 110 and the respective functional surface of the associated first clamping element 120 have an open position in which a gap having a width in axial direction extends between the two functional surfaces and a closed position in which the first functional surface of the end plate 110 abuts on the functional surface of the first clamping element. Any hair that may have been clamped in between the functional surfaces in their closed position will eventually be plucked from the skin. The functional surfaces of the end plate 110 may be arranged in an axially displaced manner such that the gaps between each of the functional surfaces and the respective associated functional surface of the clamping elements do not overlap in axial direction or overlap only to a certain degree, e.g. less than 20% of the axial width. The clamping head 100 of the shown embodiment further comprises a set of five additional clamping elements 150A, 150B, etc. (i.e. a first additional clamping element, a second additional clamping element . . . ) that are also circumferentially and axially displaced from each other. As will be explained with reference to FIG. 5 below, the centre plate 140 may then have five functional surfaces (i.e. a first functional surface, a second functional surface, etc.) that are also circumferentially and axially displaced. All what was said with reference to the functional surfaces of the end plate 110 and of the functional surfaces of the clamping elements 120A, 120B, etc. shall apply mutatis mutandis to the functional surfaces of the centre plate 140 and to the functional surfaces of the additional clamping elements 150A, 150B, etc.

Figure 8:
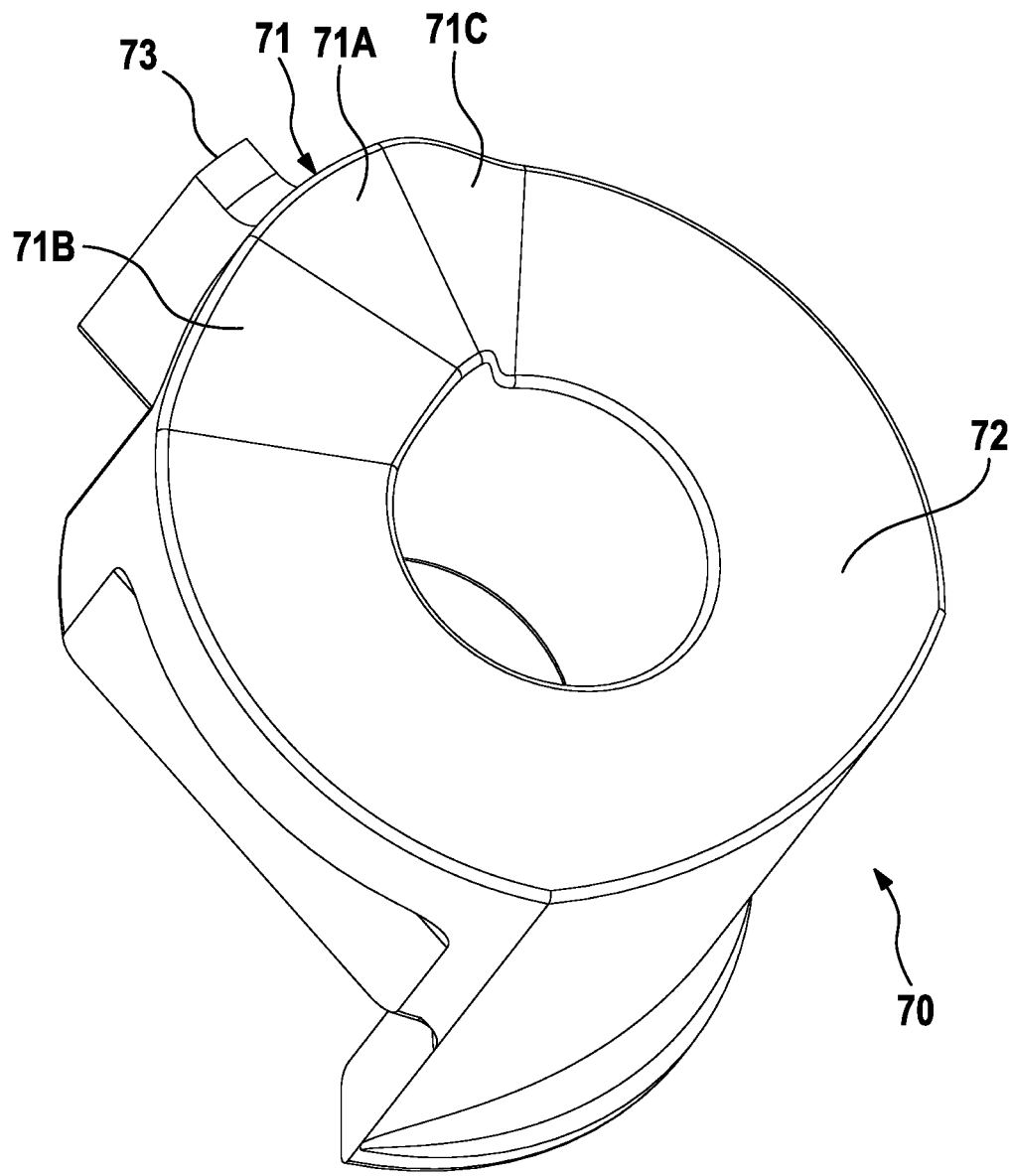
FIG. 8 is a perspective view onto a pressure plate as may be used in an epilator or an attachment for an epilator in accordance with the present disclosure.

As will be explained in more detail further below, each clamping element may be associated with an actuator (i.e. the first clamping element 120A is then associated with a first actuator 130A, the second clamping element 120B with a second actuator 130B, etc. and the first additional clamping element 150A with a first additional actuator 160A . . . ). In the shown embodiment, the actuators are rod-like elements that are guided by the closure element 170 such that they extend in axially direction beyond the closure element 170 towards the pressure plate 70. As also will be explained in more detail further below (FIG. 8), the pressure plate 70 may have a functional surface that faces the ends of the actuators distal to the associated clamping elements, which ends extend beyond the closure element 170. The functional surface of the pressure plate 70 may have a axial projection 71 that projects in axial direction towards the ends of the actuators. When being rotated together with the axle 40, the actuators are arranged such the ends of the actuators may at least intermittently get into sliding contact with the functional surface of the pressure plate 70, in particular, they are arranged to slide at least partly over the axial projection 71. The actuators and thus the associated clamping elements are then axially moved towards the end plate 110 (or the centre plate 140) such that the functional surface of the respective clamping element moves towards the respective face-to-face arranged functional surface of the end plate 110 (or the centre plate 140) until the gap between the two functional surfaces is closed and the face-to-face arranged functional surfaces abut on each other. The resilient element 60 may then also be compressed in axial direction and would then provide the clamping force with which the abutting functional surfaces clamp hairs. The first stopper element, which is fixed in axial relationship with the axle 40 and against which the resilient element 60 abuts in axial direction then provides the force transmission closure functionality, i.e. the first stopper element needs to be arranged to withstand the forces occurring in the process of successively closing the associated functional surfaces of the clamping elements and the end plate (or centre plate) without any major deformation or destruction.

Figure 3B:
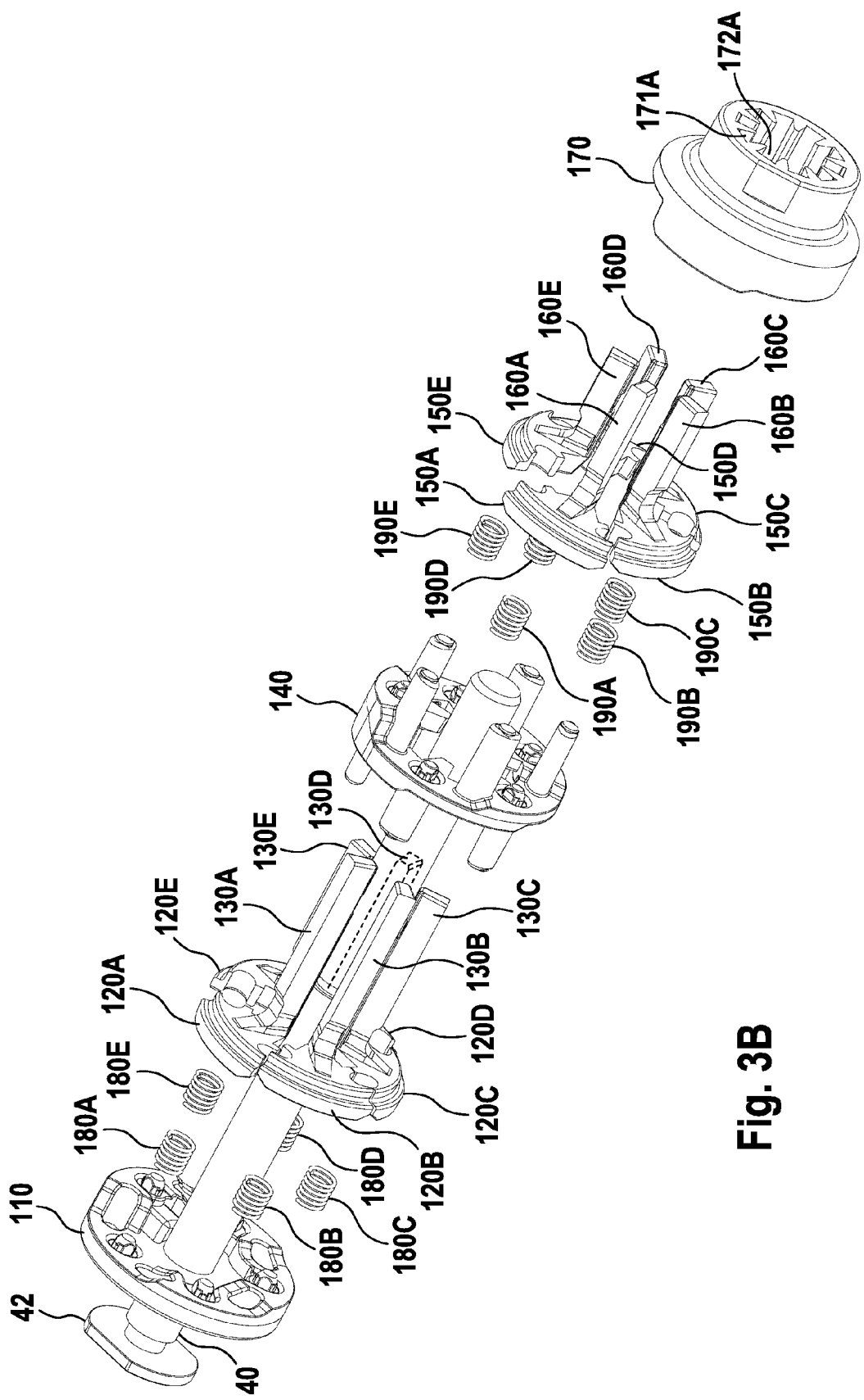
FIG. 3B is an exploded view of the clamping head shown in FIG. 3A.

FIG. 3B is a perspective exploded view of a clamping head 100. In some embodiments, a second stopper element 42 is fixedly connected with the axle 40, which second stopper element 42 on the one hand provides a stopper for the end plate 110 such that the end plate 110 essentially flushes with the respective end of the axle 40 and on the other hand provides an engagement element that couples with a depression in the end plate 110 in a form-fit manner (alternatively or additionally in a force-fit manner) and thus serves to rotate the end plate 110 when the axle 40 is driven into rotation. In some embodiments, the end plate itself may be directly fixed onto the axle (e.g. by welding, gluing, etc.), may be integral with the axle or may be secured by a stopper element at the axle such that any axial movement is effectively inhibited. The end plate 110 has a set of circumferentially and axially displaced functional surfaces 111A, 111B, 111C, 111D, and 111E (obviously, in an embodiment with only one clamping element, the end plate would have only one functional surface; in embodiments with two clamping elements, the end plate has two functional surfaces, which may be circumferentially and/or axially displaced from each other, etc.). Below the center of the first functional surface 111A a cavity or depression 112A may be arranged for receiving a spring element 180A and similarly such cavities may also be realized below the other functional surfaces. At least one of the oppositely arranged cavities or depressions may comprise a central pin onto which the respective spring element may be slid. Alternatively, at least in one case only such a central pin may be present instead of a cavity or depression. A set of five clamping elements 120A, 120B, 120C, 120D, and 120E is arranged such that a functional surface of each of the clamping elements is arranged face-to-face with one of the functional surfaces of the end plate 110. More generally, a spring element may be arranged between the end plate and the first clamping element to keep these parts in an open position until a closing force overcomes the force of the spring element.

Figure 6:
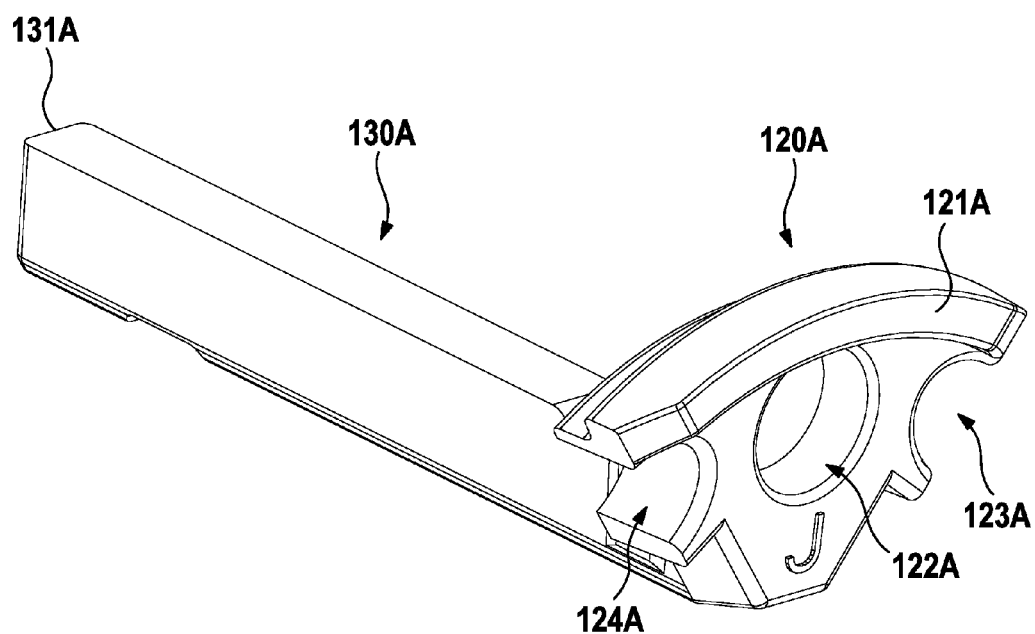
FIG. 6 is a perspective view onto a clamping element and an associated actuator realized as an integral element as may be used in an epilator or an attachment for an epilator in accordance with the present disclosure.

With reference to FIG. 6, a cavity or depression 122A may be provided below the functional surface of each of the clamping elements such that this cavity is arranged face-to-face with (i.e. oppositely to) a respective cavity in the end plate 110. Each pair of oppositely arranged cavities may receive ends of one of the spring elements 180A, 180B, etc. The spring elements 180A, 180B, etc. are provided to keep the face-to-face arranged functional surfaces in an open position, i.e. in a position where a gap having an axial width extends between the functional surfaces, as long as the respective clamping element is not biased with a closing force, as will be explained further below. The axial gap width may be in the range of between about 0.05 mm to about 2.0 mm. In the shown embodiment, each of the clamping elements 120A, 120B, 120C, 120D, and 120E is associated (in a one-to-one sense) with a respective actuator 130A, 130B, 130C, 130D, and 130E.

Here, the clamping elements and the respective associated actuators are each realized as an integral element, which may be manufactured by plastic injection molding, in particular from a reinforce plastic material, e.g. a glass fiber filled plastic material. This shall not exclude that in some embodiments, at least some of the clamping elements and the respective associated actuators are realized as separate parts.

A centre plate 140 may be arranged between the end plate 110 and a closure element 170. The centre plate 140 may have a set of five axially extending pins 148A, 148B, 148C, 148D, and 148E of which at least one may be arranged to be press-fitted in a respective cavity in the end plate during assembly. The centre plate 140 also has a set of five axially extending additional pins 149A, 149B, 149C, 149D, and 149E of which at least one is arranged for being press-fitted in a respective cavity in the closure element 170 during assembly. Each axially extending (additional) pin is arranged to cooperate with a lateral, semi-circular cut-out of two neighboring (additional) clamping elements and thus also serves as guiding structure for the (additional) clamping elements. The centre plate 140 is thus in the shown example integrally realized with axially extending connection structures for connecting the closure element with the centre plate and the centre plate with the end plate. In some embodiments, the axially extending (additional) pins may be realized integrally with the end plate (closure element), whereas in some embodiments, the axially extending pins may be arranged as separate parts. In some embodiments, at least one of the axially extending (additional) pins may integrally realized with the end plate or the centre plate (closure element) and at least one axially extending pin may be a separate part.

As has been described for the assembly of end plate 110 and the clamping elements 120A-120E, the centre plate 140 may comprise five from each other axially and circumferentially displaced functional surfaces that are arranged face-to-face with respective functional surfaces of a set of five additional clamping elements 150A, 150B, 150C, 150D, and 150E. Spring elements 190A, 190B, etc. are again received in pairs of (potentially circular) cavities (which may in particular comprise a central pin) realized below the functional surfaces (i.e. at a radial position closer to the axle 40 than the respective functional surface) such that the face-to-face arranged functional surfaces are kept in an open position in which a gap having an axial width extends between the functional surfaces as long as the respective additional clamping element is not biased with a clamping force. Again, each of the additional clamping elements 150A, 150B, 150C, 150D, and 150E is associated with one additional actuator 160A, 160B, 160C, 160D, and 160E and again the additional clamping elements and the associated actuators may be in each case realized as an integral element instead of being separate elements. The set of additional clamping elements is circumferentially offset to the set of clamping elements (here: by an angle of 36 degrees, i.e. half the angular width of a clamping element) such that the actuators and the additional actuators are alternately arranged in circumferential direction.

The closure element 170 comprises ten essentially rectangular and axially extending guiding structures 171A, 171B, etc. and 172A, 172B, etc. for guiding the actuators and the additional actuators. In some embodiments, at least one of the actuators has a circular, oval, triangular, etc. cross section instead of a rectangular cross section. In some embodiments, at least two actuators have a different cross sectional form. The length of the actuators and of the additional actuators is chosen such that in an unbiased condition they all extend to the same axial position (i.e. beyond the closure element towards the pressure plate).

Figure 3C:
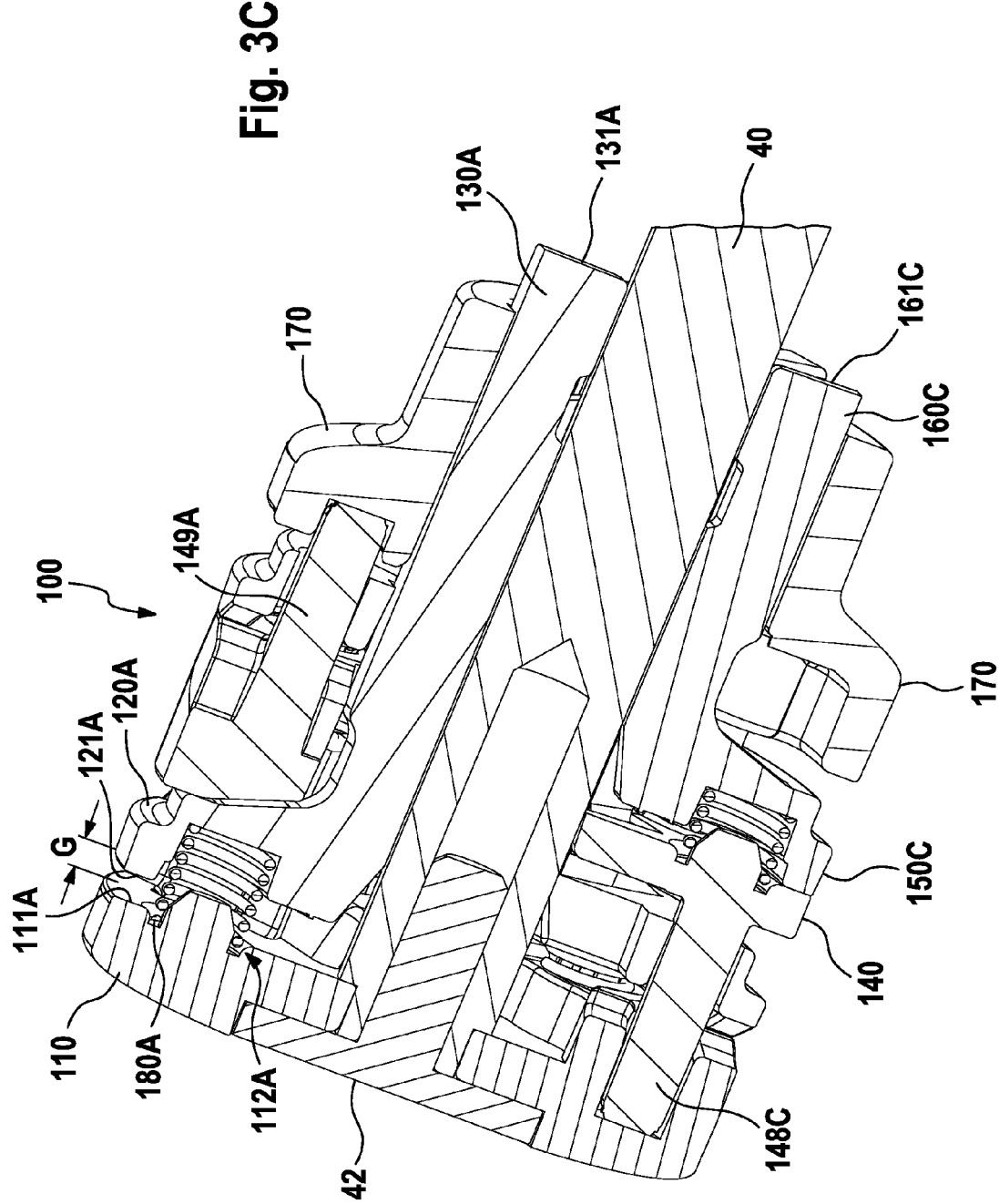
FIG. 3C is a depiction of a longitudinally cut open clamping head as shown in FIG. 3A.

FIG. 3C is a longitudinal cross-sectional cut through the assembled clamping head 100 mounted on the axle 40. The same features as described in FIGS. 3A and 3B are assigned with the same reference numerals.

As will be explained in more detail further below, the pressure plate 70 has a fixed angular position around the axle when the axle is driven into rotation and thus the pressure plate 70 does not rotate together with the axle (the pressure plate 70 may be arranged to have a different angular position around the axle when the rotation occurs in clockwise direction than when the rotation occurs in counterclockwise direction so that a certain degree of freedom of rotation around the axle of the pressure plate 70 may be given). As can be seen from FIG. 3A together with FIG. 8, the circumferential position of an axial projection 71 on the pressure plate 70 determines the position at which the clamping elements are moved from the open position into a closed position, in which the face-to-face arranged functional surfaces of one of the clamping elements and of the end plate (or of one of the additional clamping elements and of the centre plate) abut on each other. The axial projection 71 has a central plateau section 71A and two ramp sections 71B and 71C that are arranged at the two circumferential sides of the plateau section 71A. As had been previously described, the axial ends 131A, 131B, etc. and 161A, 161B, etc. of the actuators 130A, 130B . . . and 160A, 160B, etc. are arranged to be in at least intermittent sliding engagement with the functional surface 72 of the pressure plate 70, i.e. the ends of the actuators at least start to get into sliding contact with one of the ramp sections 71B and 71C, respectively, of the axial projection 71 depending on the rotation direction. In some embodiments, the ends of the actuators may always be in constant sliding contact with the functional surface 72 of the pressure plate, while in other embodiments, the axial ends of the actuators may be arranged such that they are not in sliding contact with the functional surface 72 outside of the axial projection 71 to reduce frictional energy loss in the system. Thus, when a distal end 131A of a first actuator 130A gets into sliding contact with a ramp section 71B, the first actuator 130A is moved towards the end plate 110 and thereby moves an associated first clamping element 120A against the biasing force of a first spring element 180A towards the end plate 110. Typically before the axial end 131A of the actuator 130A reaches the plateau section 71A, the face-to-face arranged functional surface of the first clamping element 130A and the first functional surface of the end plate 110 are in the closed position, i.e. they abut on each other. When the actuator further moves along the ramp section 71B (or 71C) towards the plateau section 71A, the pressure plate is pushed towards the resilient element 60 (see FIG. 3A) and the resilient element is compressed and thus clamping force builds up that is then constant while the axial end 131A of the first actuator 130A slides over the plateau section 71A. Hairs clamped in between the closed functional surfaces will push the functional surfaces slightly open; this leads to an additional compression of the resilient element 60 and thus further increases the clamping force. The face-to-face arranged functional surfaces are in the closed position as long as the end 131A of the first actuator 130A slides over the plateau section 71A. The plateau section 71A spans an angular range that is chosen such that hairs clamped in between the functional surfaces are plucked from the skin while the clamping head rotates relative to the skin. The functional surfaces are opened again by the spring force of the spring element 180A when the axial end 131A of the first actuator 130A slides downwards along the second ramp section 71C (or 71B) and the opening force becomes larger than any closing force (or the closing force vanishes).

Figure 4:
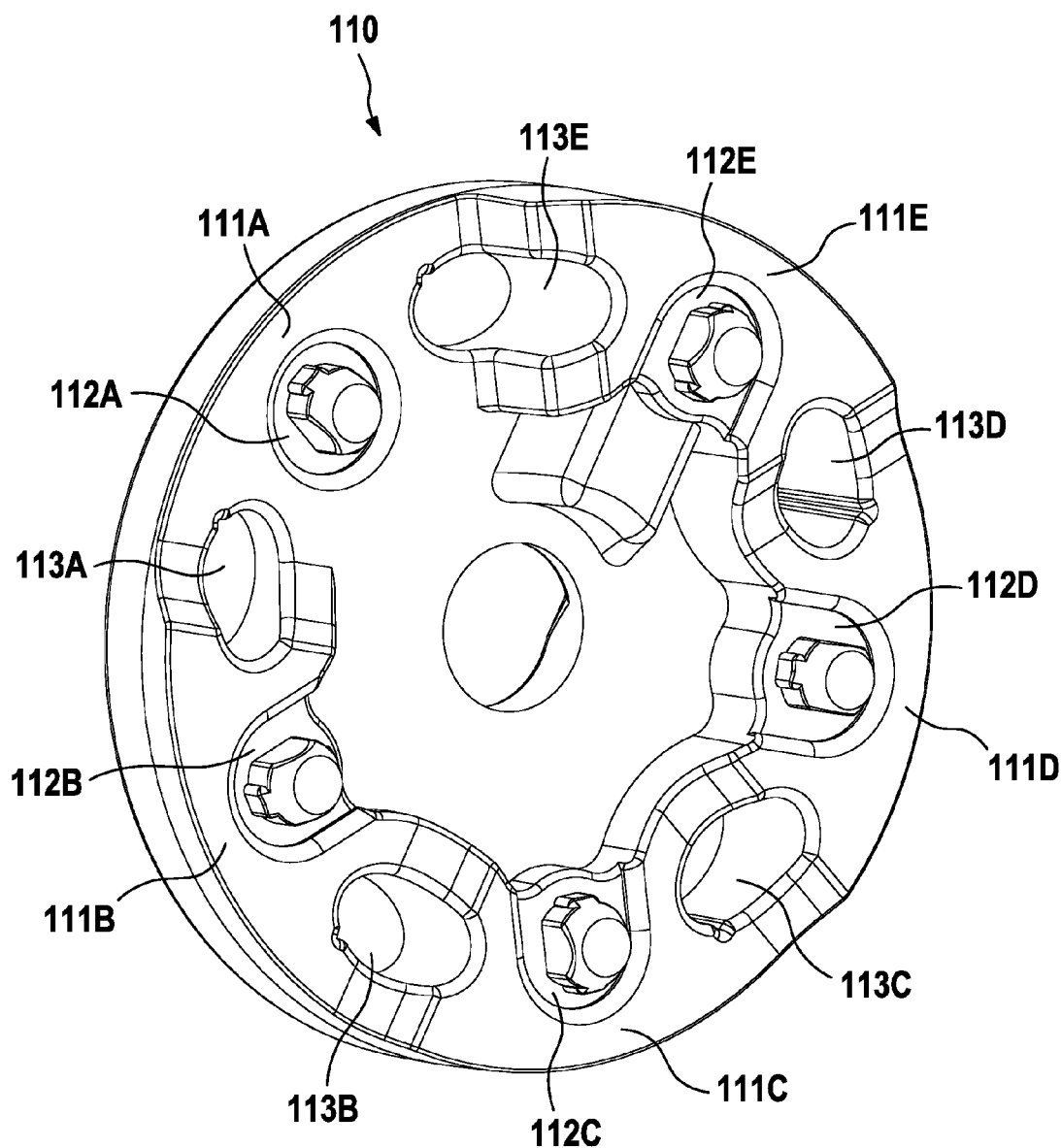
FIG. 4 is a perspective view onto an end plate as may be used in an epilator or an attachment for an epilator in accordance with the present disclosure.

FIG. 4 is a perspective view onto the functional side of an example embodiment of an end plate 110. The end plate 110 has a first functional surface 111A arranged on the radial outer edge of the functional side. Radially below the first functional surface 111A a first cavity 112A is provided for receiving a first spring element arranged between the end plate 110 and a first clamping element 130A (see FIG. 6) such that a functional surface of the first clamping element 130A is kept at a distance to the first functional surface 111A of the end plate 110 as long as the first clamping element 130A is not biased with a clamping force towards the end plate 110. As shown in FIG. 4, the first cavity may have a central axially extending projection for holding and/or centering the first spring element 180A. The end plate 110 may also have a first pin cavity 113A for receiving an axially extending pin 148A of a centre plate 140 (see FIG. 5). Obviously, the pin cavity (or the pin cavities) is optional and further, if provided, the pin cavity (cavities) may also receive a pin (pins) from a closure element. The end plate 110 may in some embodiments have two or more functional surfaces 111A, 111B . . . that may in particular be arranged circumferentially displaced at the radial outer edge of the end plate 110 and the functional surfaces may optionally (alternatively or additionally) be arranged on different axial levels, i.e. the functional surfaces be arranged axially displace. In the shown example embodiment, the end plate 110 has five functional surfaces 111A, 111B, 111C, 111D, 111E and respectively five cavities 112A to 112E for receiving spring elements and also five pin cavities 113A to 113E. While the functional surface may each span an angular width of 72 degrees, each functional surface may effectively only span a smaller angular width (e.g. 60 degrees) because of e.g. manufacturing reasons not allowing 90 degree walls between the different axial levels. In some embodiments, the functional surfaces may span different angular widths.

Figure 5:
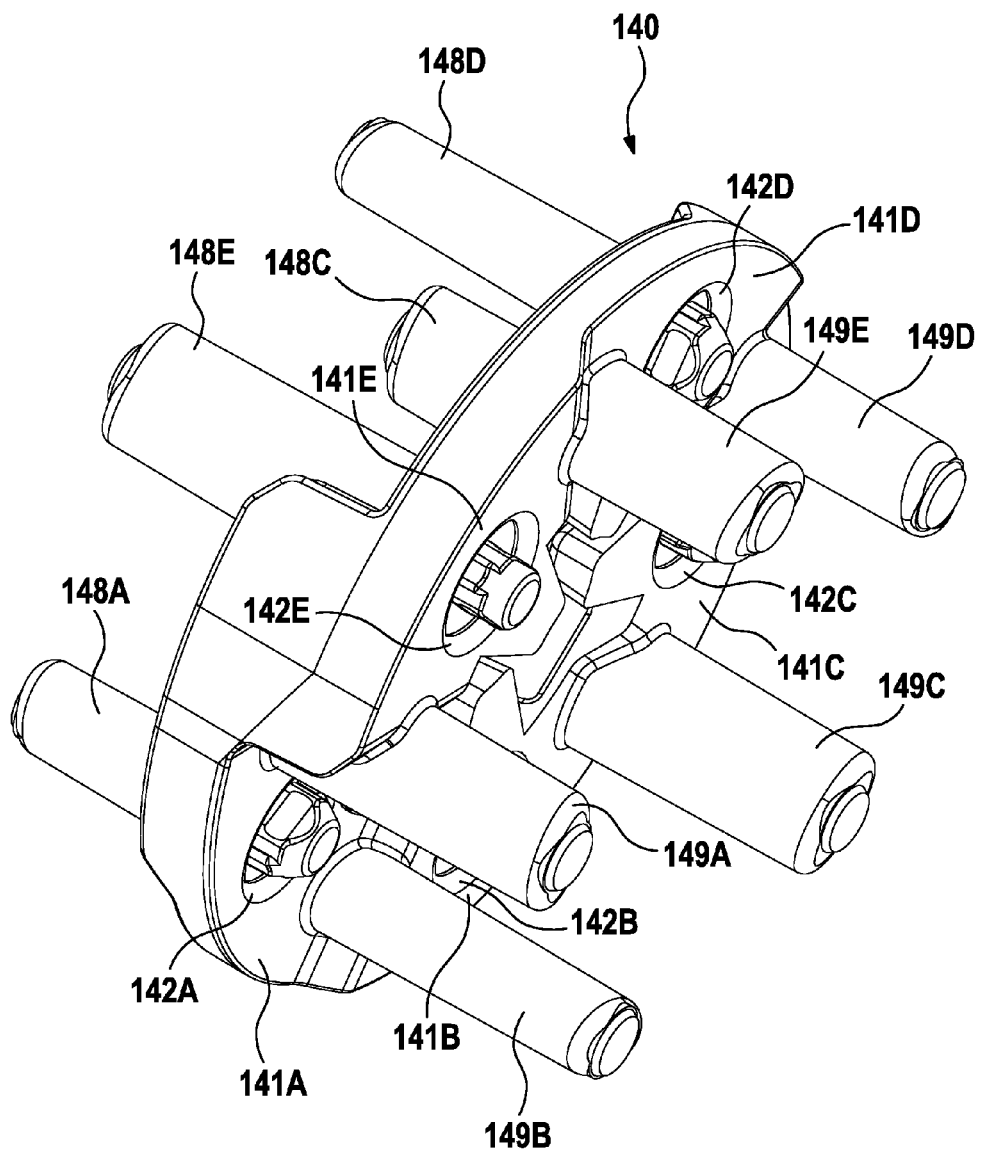
FIG. 5 is a perspective view onto a centre plate as may be used in an epilator or an attachment for an epilator in accordance with the present disclosure.

FIG. 5 is a perspective view onto an example embodiment of a centre plate 140 that may be used in some embodiments of epilators or attachments for epilators in accordance with the present disclosure. A centre plate 140 may in particular be used to facilitate usage of a set of additional clamping elements. The centre plate 140 may have a first axially extending pin 148A having an end section arranged for being received by a respective pin cavity 113A in an end plate 110 (see FIG. 4). The centre plate 140 may in particular have two or more axially extending pins 148A, 148B, etc. having end sections arranged for being received by respective pin cavities in the end plate 110. In the shown embodiment, the centre plate 140 has five axially extending pins 148A to 148E. At least one of the end sections of the axially extending pins and the respective pin cavity may be arranged for a press fit so that the end plate 110 and the centre plate 140 are relative strongly joined together in the assembled state. The centre plate 140 may additionally have a first axially extending additional pin 149A having an end section arranged for being received by a respective cavity 173A of a closure element (see FIG. 7). Again, the centre plate 140 may in particular have two or more axially extending additional pins 149A, 149B, etc. having end sections of which at least one may be arranged for being received by respective pin cavity in a closure element. In the shown embodiment, the centre plate 140 has five axially extending additional pins 149A to 149E. It is noted that, depending on available construction volume, one or several further centre plates could be sequentially arranged to facilitate even more additional sets of additional clamping elements.

It is stated that the above described axially extending (additional) pins are part of an axially extending connection structure that axially and angularly locks the closure element with respect to the end plate. As has been shown and explained, the axially extending connection structure may also axially and angularly lock a centre plate arranged between the end plate and the closure element. In some embodiments, the axially extending connection structure that connects either the end plate with the closure element or the end plate with a centre plate and the centre plate with the closure element may be realized as individual axially extending pins instead as being realized integrally with at least one of the end plate, centre plate, an/or closure element. In some embodiments, at least one axially extending pin may be realized as an integral element and at least one axially extending pin may be realized as an individual (i.e. separate) pin.

The centre plate 140 may comprise a first functional surface 141A at a radial outer edge of a functional side of the centre plate 140, which first functional surface 141A may be arranged face-to-face with a functional surface of a first additional clamping element 150A (see FIGS. 3A-3C). The centre plate 140 may in particular comprise two or more functional surfaces 141A, 141B, etc. that may in particular be circumferentially and/or axially displaced from each other. As was explained for the end plate, the centre plate 140 may comprise one or more cavities 142A, 142B, etc. each arranged radially below a functional surface for receiving a spring element 190A, 190B, etc. (see FIG. 3B).

FIG. 6 is a perspective view onto a first clamping element 120A and a first actuator 130A associated with the first clamping element 120A. In the shown embodiment, the first clamping element 120A and the first actuator 130A are integrally manufactured, e.g. by a plastic injection molding process in which in particular a filled plastic material may be used. In other embodiments, a first actuator is separate from a first clamping element. The first clamping element 120A has a functional surface 121A that in the assembled clamping head 100 (see FIGS. 3A-3C) is arranged face-to-face with a first functional surface 111A of an end plate 110 (see FIG. 4). The first clamping element 120A may comprise a cavity 122A for receiving an end of a spring element 180A (see FIGS. 3B, 3C). The first clamping element 120A may comprise cut-outs 123A and 124A at circumferential sides of the first clamping element 120A, which cut-outs 123A, 124A may have e.g. an approximately semi-circular shape. The cut-outs 123A, 124A may receive axially extending pins for stabilization and/or guidance of the first clamping element 120A in radial direction. The first actuator 130A has an end 131A that is distal to the first clamping element 120A. This distal end 131A is arranged in the assembled clamping head for at least intermittent sliding contact with a functional surface 72 of a pressure plate 70 as had been explained with reference to FIGS. 3A-3C and FIG. 8.

Figure 7:
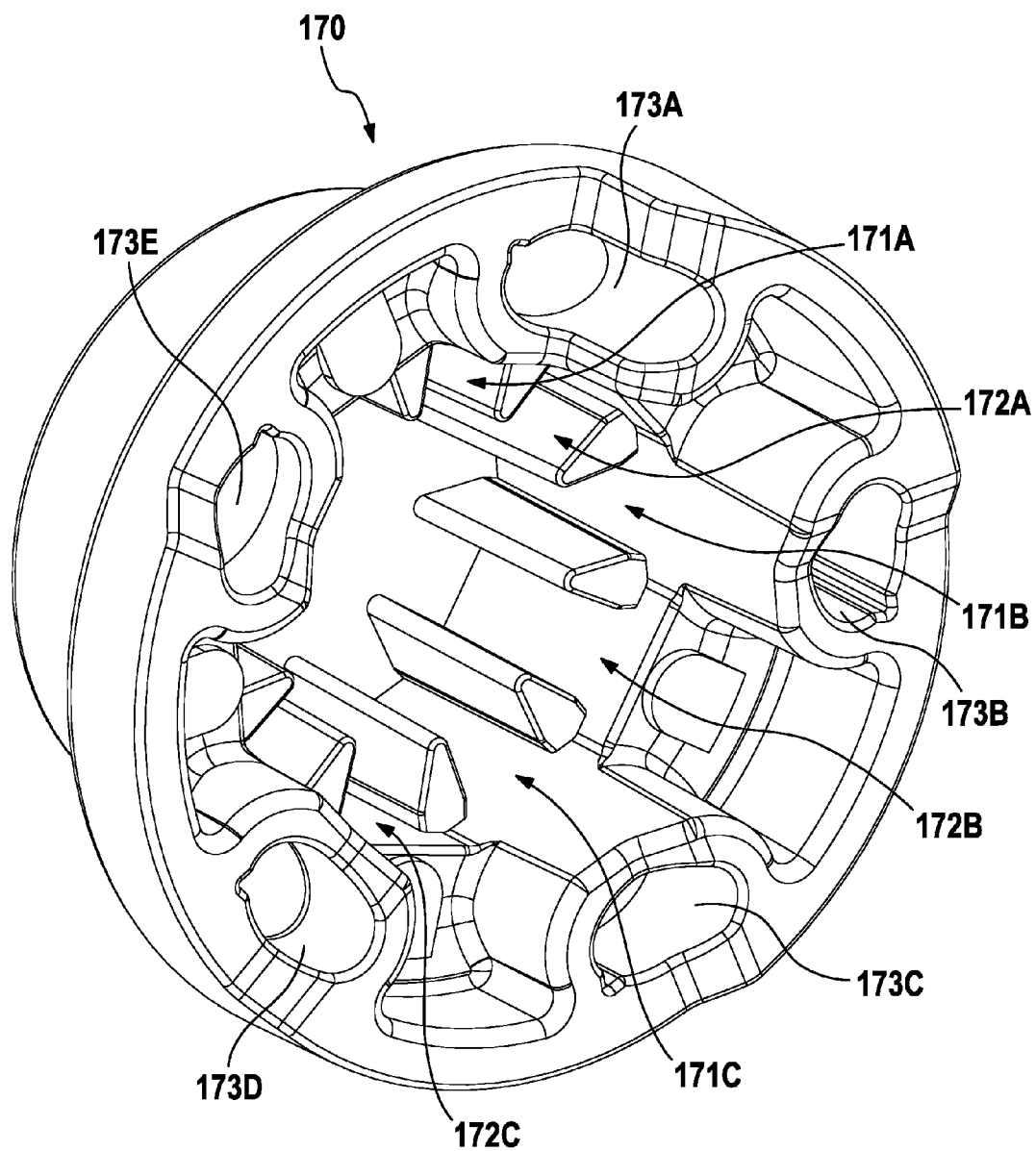
FIG. 7 is a perspective view onto a closure element as may be used in an epilator or an attachment for an epilator in accordance with the present disclosure.

FIG. 7 is a perspective view onto a front side of an example embodiment of a closure element 170, where the front side is the side that in the assembled state of the clamping head faces the centre plate (or, in embodiments without a centre plate, faces the end plate). The closure element 170 may comprise one or more pin cavities 173A, 173B, etc. for receiving axially extending pins provided by a centre plate or an end plate. Obviously, the arrangement may also be reversed and the closure element 170 may have axially extending pins or may have a combination of pin cavities and axially extending pins. The closure element 170 may have at least a first axially extending guiding structure 171A that may have an essentially rectangular cross section for receiving and guiding a first actuator 130A. The closure element 170 may have two or more axially extending guiding structures 171A, 171B, etc. for receiving actuators 130A, 130B, etc. In some embodiments, the closure element 170 may comprise additional axially extending guiding structures 172A, 172B, etc. that may be alternately arranged with the axially extending guiding structures 171A, 171B, etc. The axially extending guiding structures 171A, 172A, 171B, 172B, etc. may in an assembled state be coaxially arranged with the axle. The axially extending guiding structures may in particular be dimensioned such that the respective actuators are guided essentially without any clearances. The walls defining the axially extending guiding structures (as well as the whole closure element and/or the other moving or guiding components of a clamping head such as the clamping elements, the actuators, and the centre plate) may optionally be made from a low friction (i.e. self-lubricating) material such as polytetrafluorethylene (PTFE).

Figure 9A:
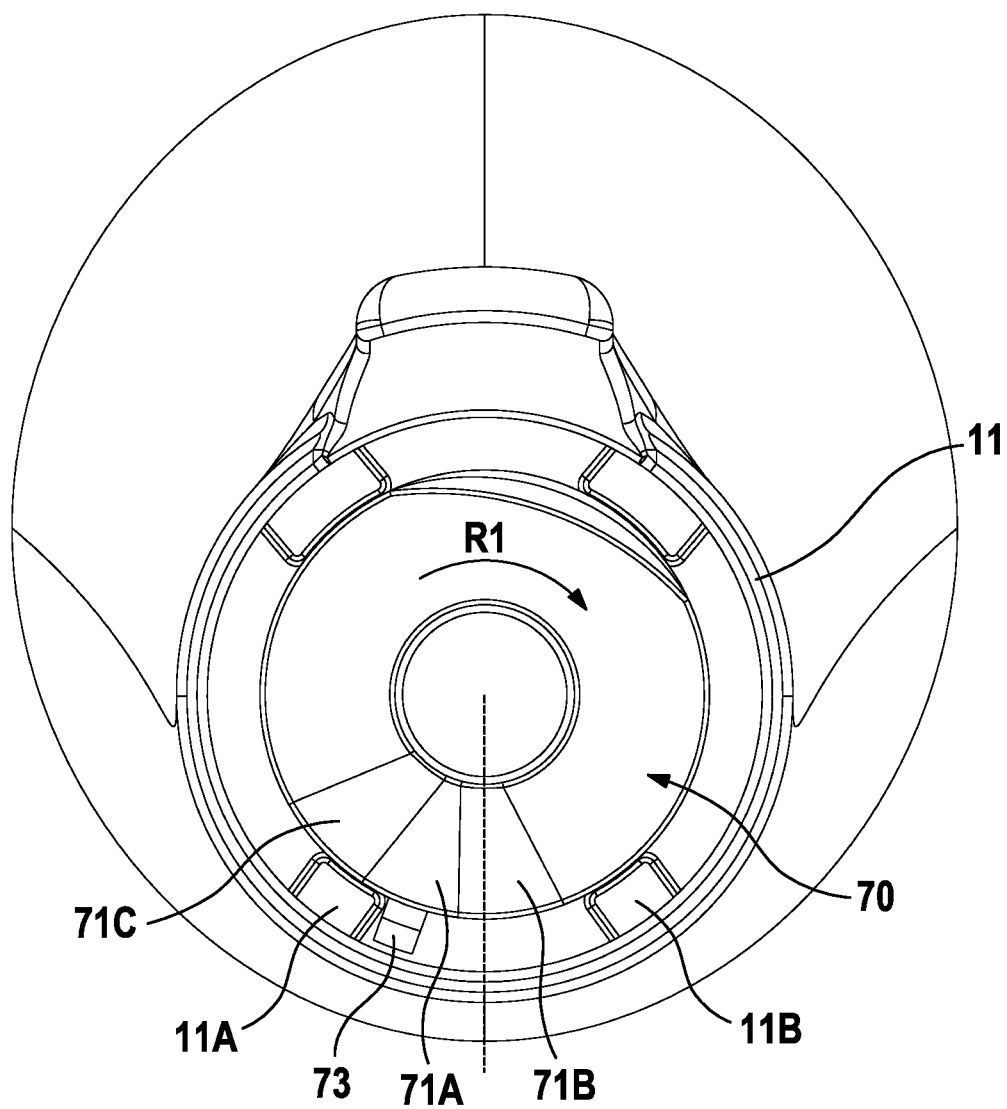
FIG. 9A is a front view onto a pressure plate mounted in a housing in a state where the axle rotates clockwise.
Figure 9B:
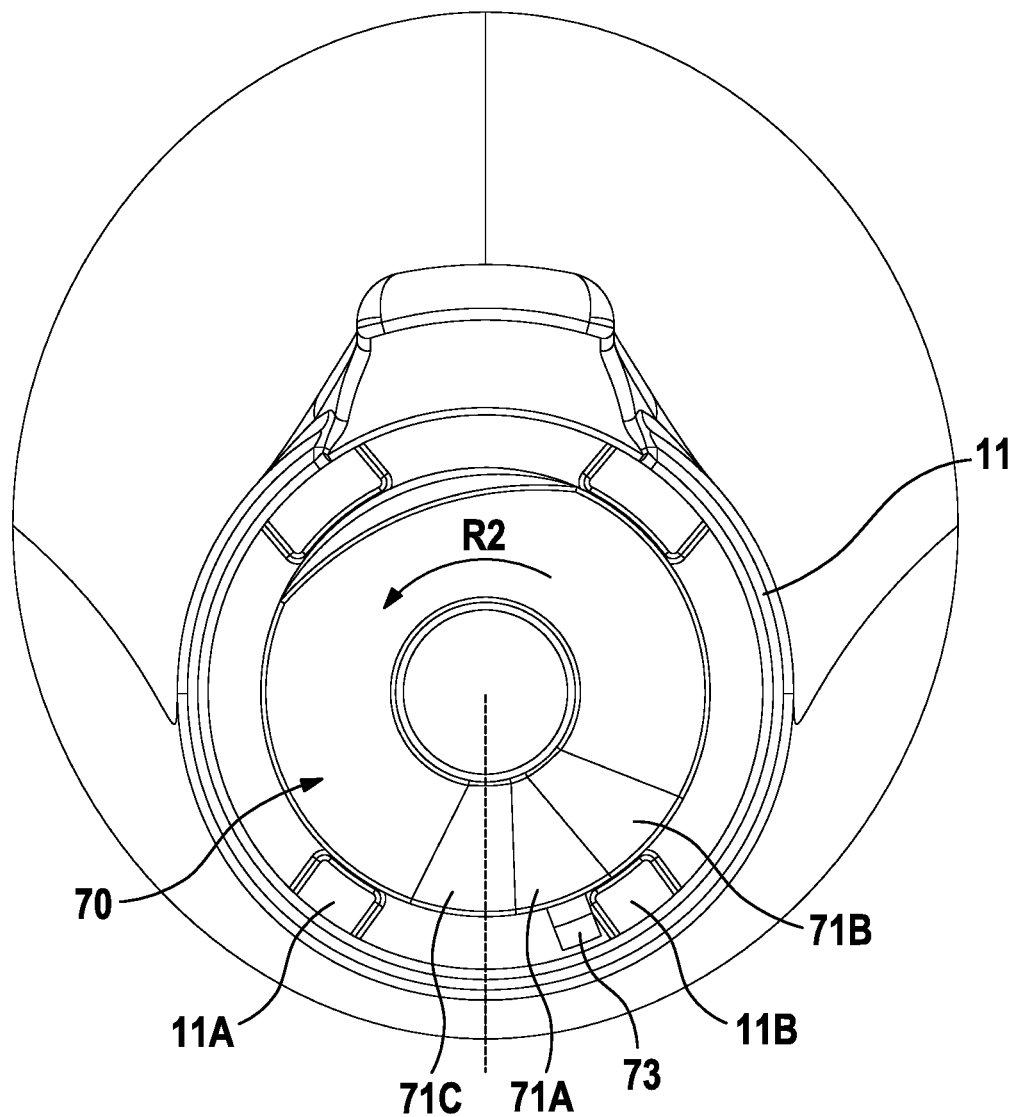
FIG. 9B is a front view onto a pressure plate mounted in a housing in a state where the axle rotates counterclockwise.

FIGS. 9A and 9B show a view onto the functional surface 72 of a pressure plate 70 mounted inside of a housing 11 of an epilator and an attachment for an epilator, where FIG. 9A shows the angular position of the pressure plate 70 for rotation of the axle 40 (and thus also of the clamping head) in clockwise direction R1 (where clockwise is here defined with respect to the view direction) and FIG. 9B shows the angular position of the pressure plate 70 in case of counter-clockwise direction of the axle 40. As had been previously explained, the epilator may have a switch for switching between clockwise and counter-clockwise rotation. This then allows switching the epilator from the right hand to left hand and vice versa, while keeping its clamping functionality. While the pressure plate 70 is essentially not coupled with the axle 40 and thus does not necessarily rotates together with the axle 40, the friction between the functional surface 72 and the distal ends of the actuator(s) drives the pressure plate to rotate. As the angular closing position of the face-to-face arranged functional surfaces shall be fixed relative to the housing of the epilator, the pressure plate 70 has a stopper element 73 that cooperates with a respective first stopper element 11A provided at the housing 11 and stops further rotation of the pressure plate 70. In case of counter-clockwise rotation, the fixation of the pressure plate 70 at the angular position shown in FIG. 9A would lead to a circumferentially shifted closing position, as the closing would not happen when the actuators slide over the second ramp section 71C but when the actuators would slide over the first ramp section 71B. Therefore, the housing 11 has a second stopper element 11B cooperating with the stopper element 73 of the pressure plate 70 at a different angular position of the pressure plate such that the closing point of the face-to-face arranged functional surfaces happens at the same angular position with respect to the housing 11. The pressure plate 70 is thus arranged to be moved between the first and the second angular positions. The particular features discussed with reference to FIGS. 9A and 9B shall also be considered as being independent from the other features discussed in the present disclosure and to thus represent an additional aspect.

In some embodiments, the pressure plate may be made from a plastic base and a metal sheet, where the metal plate realizes at least a part of the functional surface of the pressure plate so that the functional surface of the pressure plate has improved wear resistance (balanced by the higher manufacturing costs). It may be considered an independent aspect of the present disclosure to manufacture a pressure plate for an epilator/attachment for an epilator comprising a clamping cylinder in such a way.

Some aspects of the present disclosure that may have been described as features in connection with other features may indeed be considered as an individual aspect of the present disclosure. This e.g. relates to the inclination angle between the holding axis of the handle and the centre axis of the attachment. As had been discussed before, such an inclination eases usage of an epilator, in particular in case the epilator comprises a clamping head providing clamping action on a side face of the epilator head (i.e. at a lateral side of the epilator). This also relates to the arrangement of the pressure plate to have different angular positions around the axle depending on whether the axle rotates clockwise or counterclockwise.

Thus in accordance with a further independent aspect, an epilator comprises a handle for being held in the hand of a user and a head section, which optionally may be arranged as a detachable attachment, comprising a clamping head arranged for driven rotation around a centre axis of an axle, wherein the handle defines a holding axis that is inclined with respect to the centre axis of the axle, where the inclination angle may be in a range of between about 1 degree to about 45 degree. All the other features described in the present disclosure may be added to this aspect.

Thus in accordance with a further independent aspect, an epilator or an attachment for an epilator comprises a pressure plate, wherein the pressure plate is arranged to have a first angular position around an axle when the axle is driven into clockwise rotation and a second angular position when the axle is driven into counterclockwise rotation. All the other features described in the present disclosure may be added to this aspect.

It is noted that all other features described in the present disclosure could be added individually or collectively to the here described independent aspects at least to the extent that this would not violate the scope and gist of these independent aspects.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A clamping head for an epilator comprising:
an axle arranged for driven movement around a centre axle axis; the axle being locked against movement in axial direction;
an end plate arranged at a first end of the axle for rotation together with the axle, the end plate having at least a first functional surface and the end plate is an outer housing part of the epilator or the clamping head for an epilator
a first clamping element having a functional surface, wherein the first functional surface of the end plate is arranged face-to-face with the functional surface of the first clamping element, and wherein the first clamping element is arranged for repeatedly being moved towards and away from the end plate such that repeatedly a closed position is obtained in which the two functional surfaces abut on each other;
a second clamping element;
a resilient element being resilient at least in axial direction and having a first end arranged against a first stopper element fixed in axial positional relationship with respect to the axle; and
a pressure plate abutting on a second end of the resilient element and having a functional surface that has an axial projection that is elevated in axial direction towards the end plate, wherein the pressure plate is arranged to have a first angular position around the axle defined by a stop of the pressure plate abutting a first stop of a housing when the axle is clockwise rotated and a second angular position around the axle defined by the stop of the pressure plate abutting a second stop of the housing when the axle is counterclockwise rotated.

2. The clamping head for an epilator in accordance with claim 1, wherein the end plate comprises several functional surfaces each being axially displaced from each other, wherein the axial displacement of the functional surfaces of the end plate is provided by different axial projections from the end plate or a different thickness of a portion of the end plate for each functional surface.

3. The clamping head for an epilator in accordance with claim 1, wherein at least a first spring element is arranged between the first clamping element and the end plate such that the first functional surface of the end plate and the functional surface of the first clamping element are biased into an open position in which a gap having an axial width extends between the two functional surfaces.

4. The clamping head in accordance with claim 1, wherein the clamping head is arranged to be attachable to and detachable from a handle of an epilator by snap elements provided on both the handle and the clamping head.

5. An attachment for an epilator comprising the clamping head of claim 1, wherein the clamping head is provided at the lateral side of the attachment.

6. An epilator comprising the clamping head in accordance with claim 1, further comprising a handle for being held in the hand of a user, wherein the handle defines a holding axis that is inclined with respect to the centre axle axis.

7. The epilator in accordance with claim 6, further comprising a drive unit having a drive axle that extends either along the centre axle axis or that extends parallel to the centre axle axis.

8. The clamping head for an epilator in accordance with claim 1, further comprising at least a first actuator associated with the first clamping element, the first actuator being arranged for getting at least intermittently into sliding contact with the functional surface of the pressure plate; and
wherein the first actuator is arranged for being movable in axial direction towards the end plate when it slides over the axial projection of the pressure plate such that the functional surface of the first clamping element and the first functional surface of the end plate are moved into the closed position.

9. The clamping head for an epilator in accordance with claim 8, comprising at least a second actuator associated with the second clamping element, which second clamping element is arranged circumferentially displaced from the first clamping element, wherein the second clamping element is also axially displaced from the first clamping element.

10. The clamping head for an epilator in accordance with claim 8, wherein at least the first clamping element and the first actuator are realized as an integral element.

11. The clamping head for an epilator in accordance with claim 9, wherein the end plate has a third functional surface arranged face-to-face with a functional surface of the second clamping element, wherein the third functional surface of the end plate is axially displaced from the first functional surface of the end plate.

12. The clamping head for an epilator in accordance with claim 9, wherein the end plate has a second functional surface arranged face-to-face with a functional surface of the second clamping element, wherein the second functional surface of the end plate is axially displaced from the first functional surface of the end plate.

13. The clamping head for an epilator in accordance with claim 8, wherein a closure element is provided that is axially and angularly locked with respect to the end plate, particularly wherein the locking is realized by an axially extending connection structure, which is realized at least in part by at least one axially extending pin.

14. The clamping head for an epilator in accordance with claim 13, comprising at least a first guiding structure for guiding the first actuator, wherein the first guiding structure is realized by a part of the axially extending connection structure such as the at least one axially extending pin.

15. The clamping head for an epilator in accordance with claim 13, further comprising a centre plate that is axially and angularly locked with respect to the end plate, by an axially extending connection structure being a part of the axially extending connection structure that locks the closure element and the end plate.

16. The clamping head for an epilator in accordance with claim 15, the centre plate further comprising at least a first functional surface arranged face-to-face with a functional surface of a first additional clamping element and the both functional surfaces being arranged for repeatedly being moved towards and away from the end plate such that repeatedly a closed position is obtained in which the two functional surfaces abut on each other.

* * * * *